United States Patent
Huiku et al.

(10) Patent No.: US 7,635,337 B2
(45) Date of Patent: Dec. 22, 2009

(54) DETERMINATION OF CLINICAL STRESS OF A SUBJECT IN PULSE OXIMETRY

(75) Inventors: Matti Huiku, Espoo (FI); Panu Takala, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 577 days.

(21) Appl. No.: 11/089,548

(22) Filed: Mar. 24, 2005

(65) Prior Publication Data

US 2006/0217615 A1  Sep. 28, 2006

(51) Int. Cl.
*A61B 5/02* (2006.01)
*A61B 5/08* (2006.01)

(52) U.S. Cl. .................... 600/484; 600/529
(58) Field of Classification Search ............. 600/484, 600/500
See application file for complete search history.

(56) References Cited

U.S. PATENT DOCUMENTS

| | | | |
|---|---|---|---|
| 2,944,542 A | 7/1960 | Barnett et al. | |
| 5,273,036 A | 12/1993 | Kronberg et al. | |
| 6,650,917 B2 | 11/2003 | Diab et al. | |
| 6,702,752 B2 * | 3/2004 | Dekker .................. | 600/484 |
| 6,709,402 B2 | 3/2004 | Dekker | |
| 6,801,798 B2 | 10/2004 | Geddes et al. | |
| 7,054,679 B2 * | 5/2006 | Hirsh .................... | 600/523 |
| 2003/0163033 A1 | 8/2003 | Dekker | |
| 2004/0193068 A1 | 9/2004 | Burton et al. | |
| 2004/0220483 A1 * | 11/2004 | Yeo et al. ............. | 600/500 |
| 2005/0010116 A1 | 1/2005 | Korhonen et al. | |

FOREIGN PATENT DOCUMENTS

| | | |
|---|---|---|
| EP | 0 553 162 | 5/1997 |
| EP | 1 273 265 | 1/2003 |
| EP | 1 440 653 A1 | 1/2004 |
| WO | WO-2004/034897 | 4/2004 |
| WO | 2005/089856 A1 | 9/2005 |

OTHER PUBLICATIONS

European Search Report dated Mar. 16, 2007.
U.S. Appl. No. 11/089,528, filed Mar. 24, 2005, Takala et al.
U.S. Appl. No. 11/089,529, filed Mar. 24, 2005, Huiku.

* cited by examiner

*Primary Examiner*—Charles A Marmor, II
*Assistant Examiner*—Christian Y Jang
(74) *Attorney, Agent, or Firm*—Andrus, Sceales, Starke & Sawall, LLP (57) ABSTRACT

The invention relates to the determination of the clinical stress of a subject. In order to bring about an uncomplicated and cost-effective method for monitoring the stress status of a subject, plethysmographic signal data is acquired from the subject and a first measurement signal is derived, which is indicative of a predetemined feature of the respiration modulation appearing in the said signal data. An index signal is then formed based on the first measurement signal and the index signal is employed as an index indicative of the clinical stress of the subject.

19 Claims, 8 Drawing Sheets

*FIG. 12a*  Group Average

*FIG. 12b*  Individual Patient Distribution

*FIG. 12c*  Partially Adapted Patient Distribution

*FIG. 12d*  Cumulative Patient Distribution

Parameter Value

FIG. 13

DETERMINATION OF CLINICAL STRESS OF A SUBJECT IN PULSE OXIMETRY

FIELD OF THE INVENTION

The present invention relates generally to the determination of the clinical stress of a subject in connection with pulse oximetry.

BACKGROUND OF THE INVENTION

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at the cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Stress is defined as a non-specific response of the body to any demand made upon it which results in symptoms such as rise in the blood pressure, release of hormones, quickness of breathe, tightening of muscles, perspiration, and increased cardiac activity. Stress is not necessarily negative. Some stress keeps us motivated and alert, while too little stress may create problems. However, too much stress can trigger problems with mental and physical health, particularly over a prolonged period of time.

The present invention relates to the determination of clinical stress, which here refers to stress induced by an underlying disease or treatment.

Sedation is a drug-induced state of a patient, during which the patient may respond normally to verbal commands or tactile stimulation and is not agitated or anxious (mild sedation), or during which the patient responds only to loud commands or tactile stimulation (moderate or conscious sedation), or during which the patient is unconscious and not easily arousable, but responds only to repeated or painful stimulation (deep or unconscious sedation). Anesthesia, in turn, is the deepest drug-induced state of sedation, during which the patient is not arousable, even by painful stimulation.

Agitation is often defined as the motor restlessness that accompanies anxiety. Mild or moderate sedation is induced to remove the agitation and to ensure optimal patient management. Optimal level of sedation varies with the stimulation affecting the patient and is often achieved, for ventilated patients, at the deepest sedation, accompanied with sufficient analgesia.

Analgesia refers to the absence of pain or loss of sensitivity to pain without unconsciousness in response to stimulation that would normally be painful.

Noxious stimuli, such as pin-pricks or inflammation exceeding a certain threshold stimulus level in nociceptive nerve fibers (nociceptors), cause a nociception, i.e. a neuronal signal or perception that denotes the induced pain or injury. Nociception is transmitted in the Central Nervous System (CNS) via several different ascending pathways causing responses that can be cortical pain responses or subcortical stress responses. NSAIDs (Non-Steroidal Anti-Inflammatory Drugs) effectively relief pain at a damaged tissue site, whereas opioids selectively affect the pain pathways in the region of the spinal cord or the brainstem. Local or regional anesthetic agents, for instance those used in epidural analgesia, block both the pain and the sensory pathways, for instance, in the spinal cord region.

Antinociception normally refers to the blocking or suppression of nociception in the pain pathways at the subcortical level. It may be described as subcortical analgesia, in distinction to preventing the perception of pain at the cortex.

The autonomic nervous system (ANS) is the 'unconscious' nervous system, which controls and regulates virtually all of our basic body functions, such as cardiac function, blood circulation and glandural secretion. The main parts of the ANS are the parasympathetical and sympathetical nervous branches. The sympathetical nervous system usually prepares us for high stress situations by speeding up the body functions. Under conditions of normal ANS regulation, the parasympathetical system restores the normal conditions in blood circulation by slowing down the heart rate. Pain, discomfort, and clinical stress may activate the sympathetical branch of the ANS and cause an increase in blood pressure, heart rate and adrenal secretions.

Electrocardiography (ECG) is a well-established method for assessing cardiac function by recording and analyzing the biopotential signals generated in the heart. Electrodes are attached on the skin of the chest with more peripheral references. The ECG is commonly used for diagnosing cardiac dysfunctions, various cardiac and circulatory diseases, and arrhythmias. Heart rate (HR), often derived from the ECG waveform, is one of the most important parameters characterizing the condition of a patient.

Respiration rate is another vital sign, which is often monitored even in basic patient care. In connection with anesthesia and sedation of ventilated patients, monitoring of the respiration is often combined with monitoring of gas exchange, which includes monitoring of inhaled and exhaled oxygen, carbon dioxide and anesthetic gases. In modern gas monitors, airway pressure (AWP) and gas flows are also measured in order to improve the safety and quality of the ventilation.

Blood pressure (maintaining blood circulation) is yet another vital sign obtained from a patient. It may be monitored either non-invasively (NIBP) or invasively (InvBP) using catheters inserted in the arteries or veins. The latter techniques are continuous and they allow a detailed monitoring of the regulation of the cardiac-circulatory and pulmonary functions.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters provide instantaneous in-vivo measurements of arterial oxygenation, and thereby an early warning of arterial hypoxemia, for example. Pulse oximeters also display a photoplethysmographic (PPG) pulse waveform, which can be related to tissue blood volume and blood flow, i.e. the blood circulation, at the site of the measurement, typically in finger or ear. The amplitude of a PPG waveform is a sensitive indicator of patient discomfort and pain, but it also reacts to non-noxious stimulations.

The photoplethysmographic signal obtained in a pulse oximeter also contains information of the respiratory function of the patient. U.S. Pat. No. 6,709,402 discloses a method for monitoring the respiration of a patient with a pulse oximeter. In this disclosure, a plethysmographic signal is processed to obtain a non-pulsatile DC signal component information, which is independent of the pulsation of the patient's heart.

The DC signal component, and its increases and decreases over time, is used to determine the respiration frequency.

Another method for extracting the respiration rate from a plethysmographic signal is disclosed in U.S. Pat. No. 6,702,752. The method first extracts heart beat-to-beat interval information from the pulsatile AC component of the plethysmographic data. The variation of this heart rate data over time, an effect called Respiratory Sinus Arrhythmia (RSA), is then utilized to obtain the respiration rate of the patient.

In general anesthesia in machine-ventilated patients, the respiration rhythm of the patient is determined by the ventilator and the respiration rate is easily monitored by following the settings of the ventilator. In post anesthesia care units (PACUs), however, patients often breathe spontaneously. The analgesic drugs affect both the nociceptive status and the respiration function of the patient, since the said drugs may depress respiration. In finding an optimal balance between a sufficient pain relief and an undisturbed respiration, monitoring of both the respiration and the stress status of the patient would be important. Especially at an early period of the recovery, the patients are influenced by analgesic drugs given during the surgery and the effective concentrations of the analgesics may vary over time. Muscle relaxants administered to the patient during the surgery may also depress the respiration in post anesthesia care.

Analysis methods using the heart rate variability (HRV) are emerging techniques for diagnosing cardiac diseases, such as lack of oxygen supply to the cardiac muscle, and for characterizing the cardiac function and the condition of the patient in general. Fast changes in the heart rate are usually caused by the parasympathetical ANS control mediated in the vagal cranial nerve. Vagal control slows down the heart beat. The slow variations (<0.15 Hz) of the heart rate are mainly associated with sympathetical activity, which accelerates the heart beat. The ratio of the fast components of the HRV to the slow components of the HRV is often called the sympatho-vagal balance, which in emergency or during intense stress turns to sympathetical dominance.

The need for reliable monitoring of the adequacy of sedation is based on the quality of patient care and on economy related aspects. Balanced sedation reduces stress and there is firm evidence that adequate sedation decreases postoperative morbidity. Prolonged stress sensitizes the central pain pathways, which increases secretion of stress hormones. It may cause exposure to unwanted side effects during the recovery from the surgery. Too light sedation causes traumatic experiences both for the patient and for the anesthesia personnel. From economical point of view, too deep sedation may cause increased costs through extra use of drugs and time, and also extended time required for care. Too deep a sedation may also cause complications and prolong the usage time of expensive facilities, such as the intensive care theater.

EP Patent 0553162 proposes a method and apparatus for assessing the depth of anesthesia by using respiratory sinus arrhythmia (RSA) as a measure of the state of the brain. The document describes a method in which a parameter indicative of clustering of the heart beat pattern is determined from the ECG waveform relative to the beginning of each respiration cycle. This parameter is then compared with a reference value calculated using a test for randomness. The parameter is then compared with the reference value to derive a measurement of the depth of anesthesia. In particular with spontaneously breathing anesthetized patients, the clustering is proportional to the RSA, which decreases with deepening anesthesia. The heart rate changes influencing the clustering are primarily controlled by the parasympathetical branch of the ANS, and therefore, the depth of anesthesia is related to the parasympathetical activity. This, however, correlates poorly with sympathetical effects, i.e. with the pain and nociception, and therefore also poorly with the adequacy of analgesia. Furthermore, the clustering takes place differently in artificial overpressure ventilation and in spontaneously breathing patients, as the heart rate always accelerates during the low pressure period of the respiration cycle and decelerates during the high pressure phase. The low pressure period occurs during the inspiration in case of spontaneously breathing patients and during the expiration in case of artificial ventilation. The proposed method works reasonably well for spontaneously breathing patients, who in addition have a large RSA, such as children, but often fails in connection with artificially ventilated older patients. Pain reduces RSA amplitudes, as does the deepening of anesthesia. As a result, a low value of clustering may suggest too deep an anesthesia, leading to a decrease in the level of hypnosis. This may, however, lead to a worse situation, as a result of which the patient may even wake up, especially if surgical stimulations are intense.

European Patent Application EP1273265 describes a simpler method for analyzing an RRI and a blood pressure (BP) time series. Furthermore, the method tries to make a clear distinction between the sympathetical and parasympathetical cardiovascular responses. The sympathetical responses correlating with the surgical stress increase the heart rate and blood pressure. The acceleration index of the heart rate and the index for the increase of the blood pressure are calculated using a filter, a kind of edge filter, which detects the increasing slopes in the values of RRI or BP, but neglects the decreasing values. The document suggests that these indices may be used as a measure of the adequacy of analgesia. However, the method lacks the specificity to noxious stimuli and detects also the variations caused by respiration and other increasing slopes resulting from normal sympathetical activation without noxious stimulation. For instance, when the patient is in light anesthesia, both the sympathetical and parasympathetical branch of the ANS is active and the indices show erroneously high values suggesting insufficient analgesia.

The above prior art technologies thus aim to describe the adequacy of anesthesia using a unidimensional concept for the depth of anesthesia. All prior art technologies that are claimed to measure the adequacy of analgesia show a considerable dependence on the level of hypnosis and, consequently, at light anesthesia without any noxious stimulations show a value that is usually associated with poor analgesia. A further drawback of the prior art technologies is that the measurement values show a considerable inter-patient variability. This makes their interpretation, i.e. the interpretation of the adequacy of anesthesia, difficult.

The prior art technologies also focus on recording the adequacy of anesthesia during the surgery and are not applicable post-operatively on spontaneously breathing patients.

International Patent Application WO 2004/034897 discloses a method and an apparatus for a plethysmographic based detection of nociception during anesthesia and sedation. In this method, predetermined pulse wave parameters are detected and compared with reference values obtained earlier by measuring the same parameters over a certain preceding time window. If a substantial change is detected in at least one pulse wave parameter, preferably in waveform amplitude, a change in another pulse wave parameter, preferably the position of the dicrotic notch, is determined. If both changes are substantial, the changes are displayed or recorded and interpreted as an indication of a nociceptive event. The method thus provides an indication of the presence of noxious stimulation. Since the method is based on detection of noxious events, i.e. short-lived changes in the signal, it cannot provide an indication of the basic level of antinociception.

U.S. Patent Application 2005/0010116 discloses a method and an apparatus for monitoring the condition of a patient under anesthesia or sedation. In this method, a mathematical index for probability of patient comfort is calculated. The probability index is obtained as a combination of physiological parameters extracted from a plethysmographic waveform, an ECG waveform, and/or electromyogram (EMG) power measured from patient forehead. Again, as in the above-referred WO application 2004/034897, the parameters in the probability index are referred to a certain reference value determined over a certain time window or at certain reference event. Since the index is only indicative of the probability of nociception, it cannot provide quantitative information of the level of nociception or of changes in the said level.

To sum up, automatic patient monitoring is important for accomplishing optimal pain relief in different phases of anesthesia or stressful treatment. However, prior art techniques are complicated as many parameters are required for the monitoring. The monitoring therefore requires measuring equipment, which is not always available in clinical set-ups.

The present invention seeks to eliminate the above drawbacks and to bring about a novel mechanism for determining the clinical stress of a patient by expanding the functionality of pulse oximeters, which are at present the standard of care for continuous monitoring of arterial oxygen saturation and therefore widely available in clinical set-ups.

SUMMARY OF THE INVENTION

The present invention seeks to provide a novel mechanism for determining the clinical stress of a patient in connection with pulse oximeters widely available in clinical set-ups. The invention further seeks to provide a cost-effective mechanism for monitoring the state of the patient in post anesthesia care areas and during stressful treatment.

In the present invention, a measurement signal is first produced, which is indicative of a predetermined feature of the respiration modulation appearing in the plethysmographic signal data obtained from a subject. The measurement signal is typically indicative of the respiration rate of the subject, but it may also be indicative of the respiration amplitude, for example. An index signal indicative of the clinical stress of the subject is then determined based on the said measurement signal. As stress changes reflect to several features of the plethysmographic signal data, one or more such features may be employed to determine the index signal. In embodiments employing only one feature, a reference measure is determined in order that the measured value may be compared against a certain scale or reference level. In case the clinical stress index is determined based on more than one feature of the plethysmographic signal data, the index may be produced by calculating a weighted average of the signals representing said features. The weights may be optimized for each patient group, and a normalization transform may be applied to at least some of the signals before supplying them to the process where the average is calculated.

Thus one aspect of the invention is providing a method for determining the clinical stress of a subject. The method includes acquiring plethysmographic signal data from a subject and deriving a first measurement signal indicative of a predetermined feature of respiration modulation appearing in the plethysmographic signal data. The method further includes forming an index signal based on the first measurement signal and employing the index signal as an index indicative of the clinical stress of the subject.

Another aspect of the invention is that of providing an apparatus for determining the clinical stress of a subject. The apparatus includes emitter means for emitting radiation at at least one wavelength, detector means for receiving said radiation at the at least one wavelength and producing at least one electrical output signal, and first signal processing means for processing the at least one electrical output signal to obtain at least one plethysmographic signal. The apparatus further includes second signal processing means for deriving a first measurement signal indicative of a predetermined feature of respiration modulation appearing in at least one of the at least one plethysmographic signal, third signal processing means for forming an index signal based on the first measurement signal, and indicator means for indicating the index signal as an indicator of the clinical stress of the subject.

As the method utilizes parameters derivable from plethysmographic signal data only, the only instrument needed is a pulse oximeter. Furthermore, the signal data of only one channel of a conventional pulse oximeter is required to determine the clinical stress index.

As the present invention allows the functionality of a conventional pulse oximeter to be expanded by a measurement that evaluates the stress status of a patient, automatic evaluation of the stress status may be introduced in clinical set-ups in a cost-effective way. This is useful not only for finding an optimal balance between a sufficient pain relief and an undisturbed respiration, but also for monitoring patients who are not able to describe their stress status normally or whose description of the their status may not be reliable. The invention therefore provides added reliability for post anesthesia care areas and for stressful therapies. Since the measurement rests on a conventional SpO2 measurement it is also easy to perform and requires no additional measures or sensors.

A still further aspect of the invention is that of providing a computer program product by means of which a conventional pulse oximeter may be upgraded to enable monitoring of the clinical stress of a subject. The computer program product includes a first program code portion configured to receive plethysmographic signal data, a second program code portion configured to derive a first measurement signal from the plethysmographic signal data, the first measurement signal being indicative of a predetermined feature of respiration modulation appearing in the plethysmographic signal data, and a third program code portion configured to form an index signal based on the first measurement signal, the index signal being indicative of the clinical stress of the subject.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 13 in the appended drawings, wherein.

DETAILED DESCRIPTION OF THE INVENTION

A pulse oximeter comprises a computerized measuring unit and a probe attached to the patient, typically to a finger or ear lobe. The probe includes a light source for sending an optical signal through the tissue and a photo detector for receiving the signal transmitted through of reflected from the tissue. On the basis of the transmitted and received signals, light absorption by the tissue may be determined. During each cardiac cycle, light absorption by the tissue varies cyclically. During the diastolic phase, absorption is caused by venous blood, tissue, bone, and pigments, whereas during the systolic phase there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

In order to distinguish between two species of hemoglobin, oxyhemoglobin ($HbO_2$), and deoxyhemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

Figure 1:
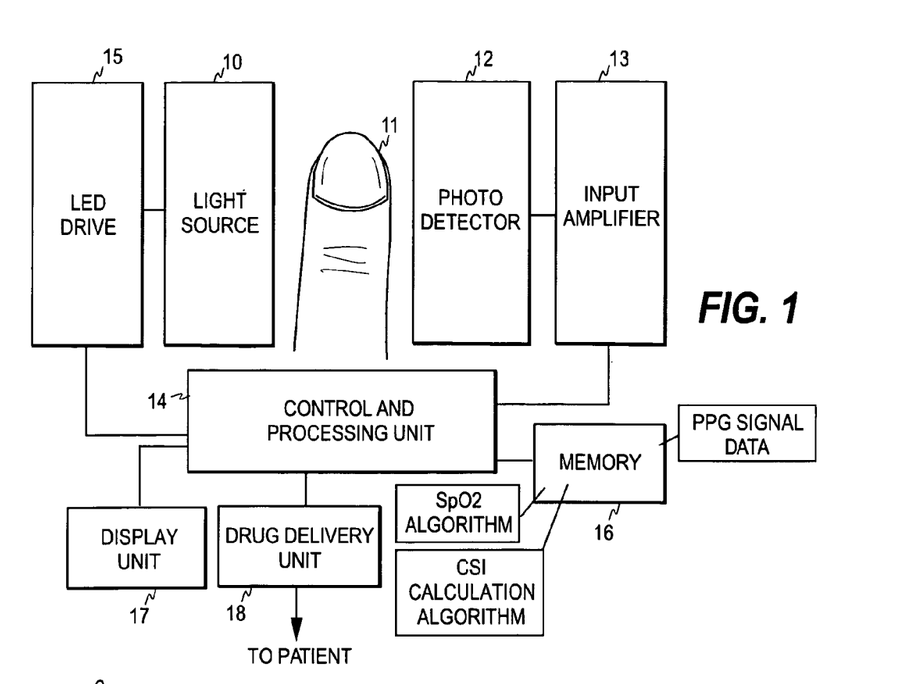
FIG. 1 is a block diagram illustrating one embodiment of a pulse oximeter according to the invention.

FIG. 1 is a block diagram of one embodiment of a pulse oximeter according to the invention. Light transmitted from a light source 10 including the LEDs passes into patient tissue, such as a finger 11. The light propagated through or reflected from the tissue is received by a photodetector 12, which converts the optical signal received into an electrical signal and feeds it to an input amplifier 13. The amplified signal is then supplied to a control and processing unit 14, which converts the signals into digitized format. The digitized signal data is then utilized by an SpO2 algorithm for determining the blood oxygen saturation. The control and processing unit executes the algorithm and drives a display 17 to present the results on the screen of the display. The SpO2 algorithm may be stored in a memory 16 of the control and processing unit.

The control and processing unit further controls a source drive 15 to alternately activate the LEDs. As mentioned above, each LED is typically illuminated several hundred times per second. The digitized PPG signal data may also be stored in the said memory before being supplied to the SpO2 algorithm.

With each LED is illuminated at such a high rate as compared to the pulse rate of the patient, the control and processing unit obtains a high number of samples at each wavelength for each cardiac cycle of the patient. The value of these samples (i.e. the amplitude of the received signal) varies according to the cardiac cycle of the patient, the variation being caused by the arterial blood, as mentioned above.

In order for variations in extrinsic factors, such as the brightness of the LEDs, sensitivity of the detector, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors.

The movement of the patient is one of the most important sources of noise and artifacts in photoplethysmographic signals and in SpO2 monitoring. Modern SpO2 algorithms are designed to tolerate motion and can detect patient motion relatively well. An example of such an algorithm is disclosed in U.S. Pat. No. 6,650,917. In sedated patients, motion is one indicator of increased pain and possibly of a too low analgesic medication.

In the present invention, a conventional pulse oximeter of the above type is upgraded with a mechanism for determining a measure indicative of the clinical stress status of the patient. The said measure is in this context termed the clinical stress index (CSI). Therefore, the digitized plethysmographic signal data is further supplied or retrieved to an index calculation process for the determination of the clinical stress index of the patient. It is sufficient that the data supplied contains the data of one channel only, i.e. the signal data of the R (red) channel or the IR (infrared) channel. However, PPG signal data formed by a combination of the two channels may also be used in the said process. Furthermore, the plethysmographic signal data employed corresponds preferably to the data of a plethysmographic signal, which is an unprocessed signal in the sense that it includes the DC component. Namely, the DC component includes respiration information and therefore valuable information may be lost if the DC component is removed from the PPG signal prior to the calculation of the clinical stress index.

Figure 2A:
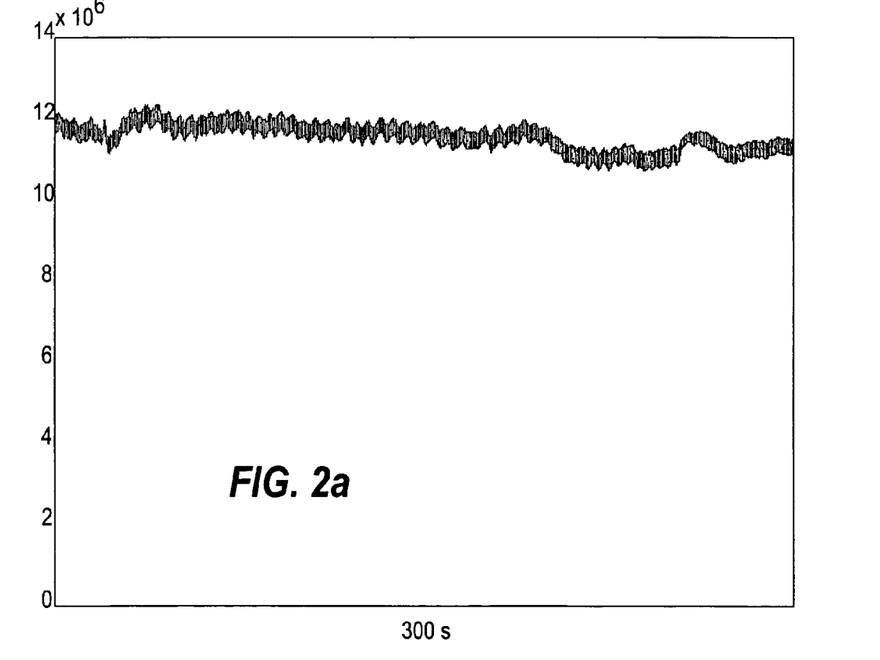
FIGS. 2a and 2b illustrate a plethysmographic signal.
Figure 2B:
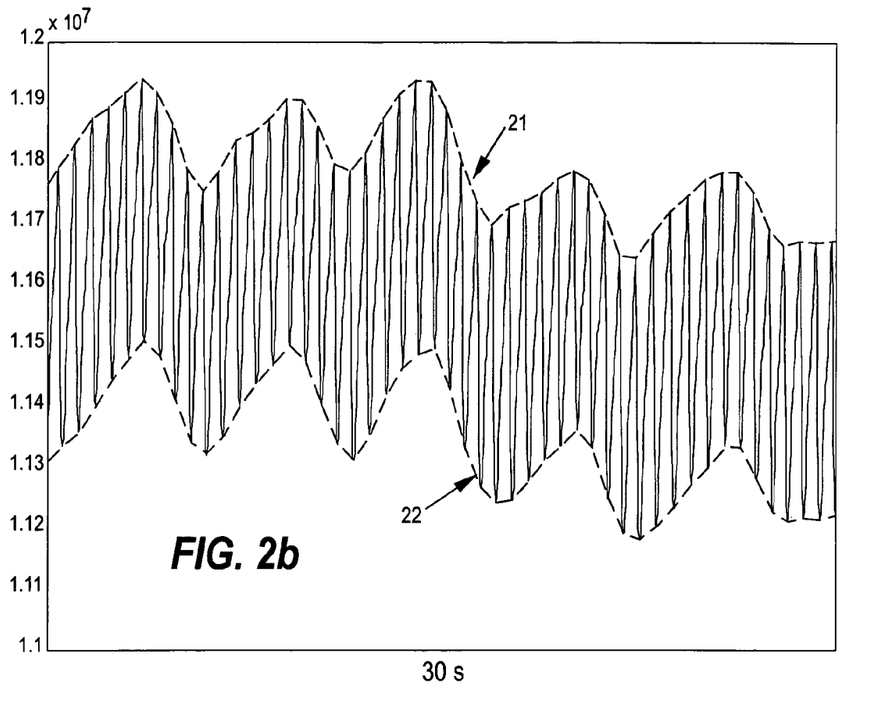

FIGS. 2a and 2b illustrate a plethysmographic signal. FIG. 2a illustrates a 5 minute interval of the signal, while FIG. 2b shows a period of 30 seconds within said 5 minute period. The modulation caused by the respiration of the patient may be seen in three different features of the plethysmographic signal. First, the amplitude of the component pulsating at the heart rate varies according to the respiration. This may be seen as a modulation in the difference of the top and bottom envelope curves, 21 respectively 22, of the signal in FIG. 2b. Second, the pulse-to-pulse interval, i.e. the interval between successive heart beats, varies according to respiration, the said interval being shorter during inspiration phases than during expiration phases. Third, the DC baseline signal, i.e. the top or bottom envelope of the plethysmographic signal, varies slowly according to the respiration. The physiological features through which respiration causes the DC component to vary are discussed in more detail in the above-mentioned U.S. Pat. No. 6,709,402.

Figure 3:
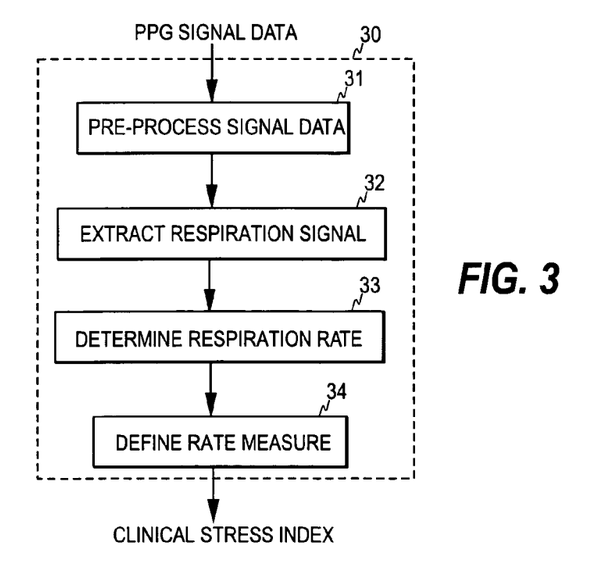
FIG. 3 illustrates one embodiment of the present invention utilizing respiration rate for determining the stress index.

FIG. 3 illustrates one embodiment of the invention, which belongs to the first group of embodiments. The PPG signal waveform data of at least one of the pulse oximeter channels is supplied to an index calculation process 30. The said signal data may be supplied to the said process simultaneously as it is supplied to the SpO2 algorithm, or the data may be retrieved from memory 16.

The recorded waveform data may first be optimized in pre-processing step 31, in which some of the frequency components of the signal may be filtered out, for example, to improve the quality of the PPG signal data. This step is not necessary, but may be performed to improve the quality of the signal data.

Next, a respiration signal is extracted from the signal data at step 32, whereby a time series is obtained, in which the respiration modulation may be seen. As described above, the respiration modulation may be seen in at least three different features of the time series of the PPG signal data, i.e. in the amplitude of the signal component pulsating at the heart rate, in the pulse-to-pulse interval of the PPG signal data, and in the DC component (baseline) of the plethysmographic signal. Therefore, the respiration signal obtained at step 32 is a time series indicative of one of the above-mentioned features or a combination of the said features.

The respiration rate of the patient is then determined based on the respiration signal (step 33). As mentioned above, the extraction of the respiration rate from PPG signal data is known as such. Any of the techniques disclosed in the above-mentioned U.S. Pat. Nos. 6,702,752 and 6,709,402 may therefore be used to obtain the respiration rate at steps 32 and 33.

Based on the respiration rate, a rate measure is then determined at step 34. The rate measure is any measure that indicates the current level of the respiration frequency as compared to the normal level of the respiration frequency of the patient. Therefore, the rate measure may be, for example, indicative of the change in the respiration rate as compared to the normal respiration rate measured previously for the same patient. Thus, step 34 allows the measured respiration rate to be compared against a certain scale or reference level in order to find out the relative level of the respiration rate. As is discussed below, step 34 may also include a normalization transform.

The time series obtained from step 34 is then employed as an index signal indicative of the clinical stress of the patient. The index may be presented on the screen of a display, such as display 17 in FIG. 1. Furthermore, the stress of the patient may be assuaged by controlling the administration of at least one analgetic or sedative to the patient based on the index values. For this purpose, the control and processing unit 14 may control a drug delivery unit 18 (FIG. 1).

In the embodiment of FIG. 3, only the respiration rate determined from the PPG signal data is employed to define the clinical stress index. However, the specifity of the index may be improved by producing an index, which is additionally based on some other features extracted from the PPG signal data. This is discussed in the following.

Figure 4:
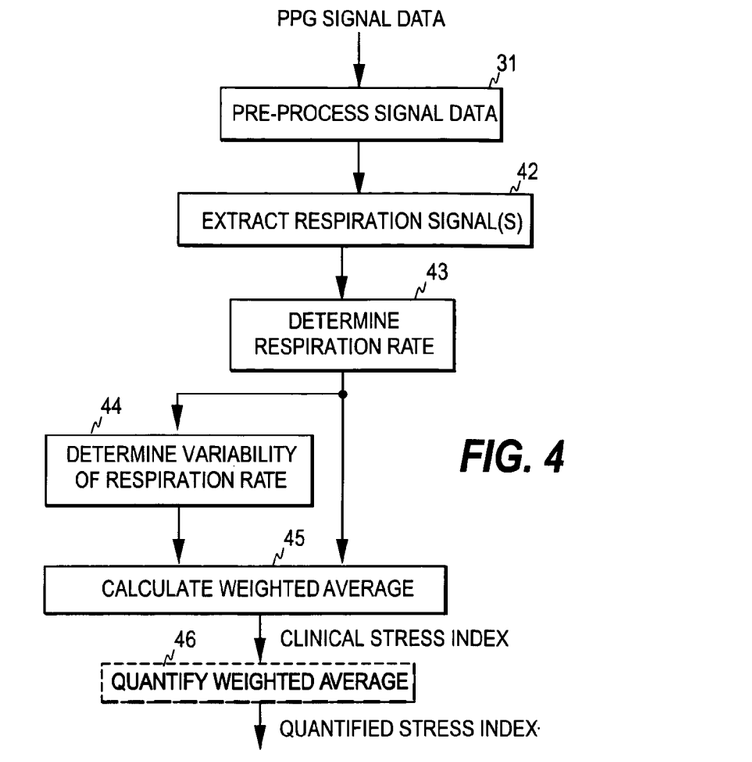
FIG. 4 to 9 illustrate further embodiments of the invention.

In the second group of embodiments, a composite stress indication is formed based on two features of the respiration modulation in the PPG signal data. An embodiment, in which the said features are the respiration rate and the variability of the respiration rate, is illustrated in FIG. 4. In this embodiment, the variability of the respiration rate is thus also taken into account by first generating, based on the time series obtained from step 43, a time series indicative the variability of the respiration rate (step 44) and then producing a composite indication based on the rate signal obtained from step 43 and the rate variability signal obtained from step 44. The composite indication may be produced by calculating a weighted average of the two signals for each data point pair obtained from the two time series. The composite indicator obtained from step 45 thus serves as the clinical stress index of the patient. The parameters used for calculating the weighted average are in this context termed PPG parameters. The use of the variability of the respiration rate as a PPG parameter is motivated by the fact that the variability of the respiration rate increases when pain and/or stress increases.

It is to be noted here that when a composite indication is formed based on more than one PPG parameter, the determination of the rate measure (step 34) may be omitted, since a reliable measure of the stress status may be obtained by optimizing the weight values for the patient group in question. In one embodiment of the invention, an optional quantification step 46 may, however, be added after step 45, as is shown by a dashed box in the figure. This optional step corresponds to step 34 of FIG. 3 in the sense that it generates a value descriptive of the magnitude of the determined average and thus sets the calculated average to a certain scale. As above, step 46 may involve the calculation of any value that indicates how the average has changed in relation to its normal value. Although not shown below, the optional quantification step may be added after the calculation of the weighted average in any of the embodiments of FIG. 4 to 8. However, as is discussed below, the quality of the stress index may be improved by applying a normalization to each PPG parameter prior to the calculation of the weighted average. Consequently, step 34 may also contain a normalization transform, i.e. the rate measure may be the normalized value of the respiration rate. As is discussed below, normalization quantifies the respective parameter individually, and it is therefore preferable to use normalization instead of step 46.

It is also possible to use the respiration rate variability as the only PPG parameter. In this case, the embodiment of FIG. 3 is modified so that step 44 of FIG. 4 is introduced between steps 33 and 34, and a variability measure is calculated in step 34 instead of a rate measure, to be able to compare the measured variability against certain reference variability, which may again be measured in advance.

Figure 5:
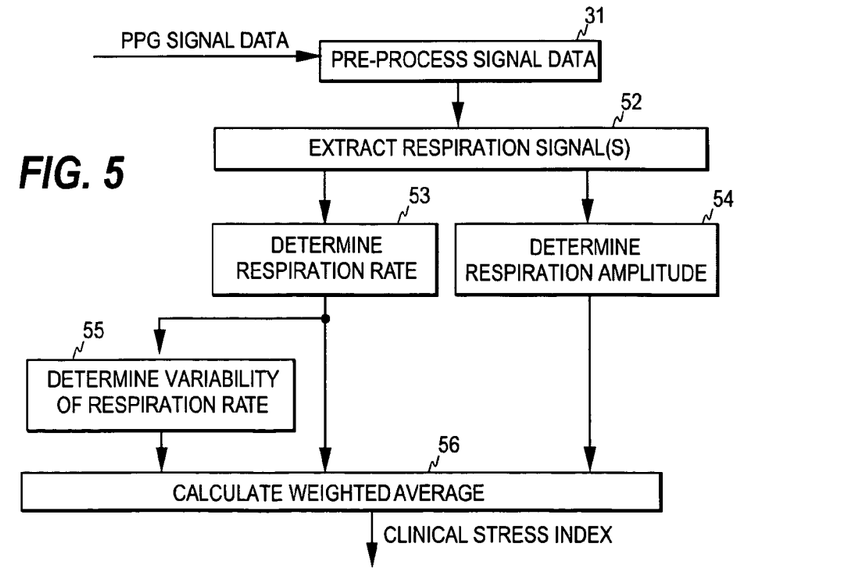

In a third group of embodiments, the clinical stress index is determined based on three PPG parameters. In one embodiment, which is illustrated in FIG. 5, the said PPG parameters are the respiration rate, the variability of the respiration rate, and the amplitude of the respiratory modulation in the signal(s), from which the respiration rate is determined. In other words, the third PPG parameter is in this case the respiration amplitude. As is shown in FIG. 5, in this case the respiration amplitude is determined based on the respiration signal at step 54, where a time series or waveform of the respiration amplitude is produced by calculating, based on the input signal, a parameter which is indicative of the amplitude of the respiration modulation in the PPG signal data. The time series corresponding to each of the three parameters are supplied to step 56, where the weighted average of the simultaneous values of the three parameters are calculated. The respiration amplitude may be used as a PPG parameter, since there is a clear correlation between changes in the stress status and the amplitude of the respiration modulation. In patients in general anesthesia the respiratory modulation decreases in stressful treatment or surgical stress. However, the nature of the correlation may depend on the technique used in steps 42/52 to extract the respiration signal from the PPG signal data.

It is to be noted here that although step 52 may correspond to steps 32 and 42, this is not necessarily the case, since various techniques may be used to obtain the respiration rate and a respiration signal indicative of the respiration amplitude is not necessarily available in steps 32 and 42. This is also the reason why corresponding steps have been denoted with different reference numerals in the figures illustrating different embodiments of the index calculation process.

It is also possible to use the respiration amplitude as the only PPG parameter. In this case, the embodiment of FIG. 3 is modified so that step 33 of FIG. 3 is replaced by step 54 of FIG. 5, and an amplitude measure is calculated in step 34 instead of a rate measure, to be able to compare the measured amplitude against certain reference amplitude, which may again be measured in advance.

Figure 6:
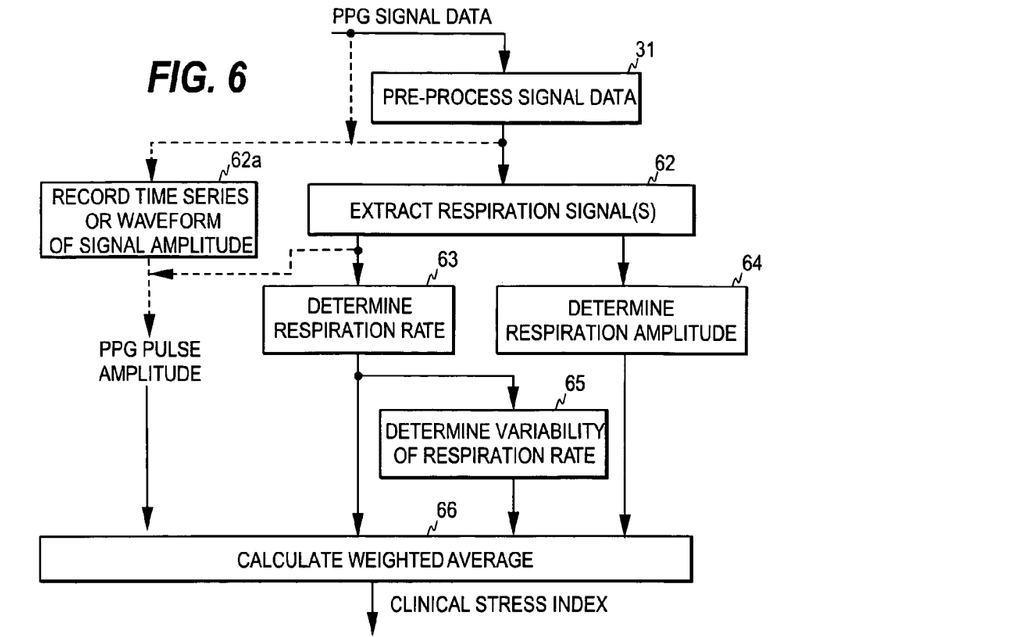

The specifity of the clinical stress index may also be improved by adding parameters describing different features of the input PPG signal data to the group of PPG parameters whose weighted average forms the clinical stress index. In a fourth group of embodiments, four PPG parameters are used to calculate the weighted average. In one embodiment of the fourth group, shown in FIG. 6, a time series representing the PPG pulse amplitude is added to the group of PPG parameters employed in the embodiment of FIG. 5. In this embodiment the weighted average is thus calculated based on four parameters: the respiration rate, the variability of the respiration rate, the respiration amplitude, and the PPG pulse amplitude. PPG pulse amplitude correlates with pain and/or anxiety so that the amplitude decreases when pain and/or anxiety increases. The weighted average is formed at step 66, which then yields the clinical stress index. Depending on the technique used in step 62 to extract the respiration signal(s), the time series or waveform representing the PPG pulse amplitude may be obtained directly from the said step. However, if the PPG pulse amplitude data is not derived in that step, the time series or waveform representing the PPG pulse amplitude may be produced in a separate step 62$a$ based on the PPG signal data input to the index calculation process or based on the pre-processed PPG signal data obtained from step 31. The different ways of obtaining the PPG pulse amplitude data are illustrated by dashed arrows in the figure.

Figure 7:
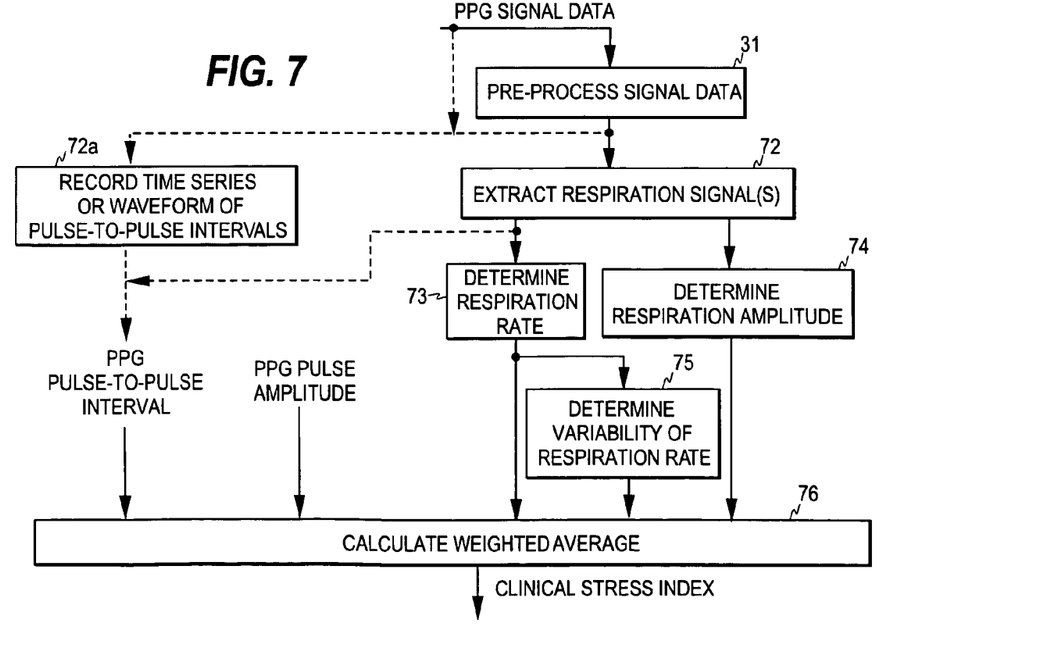

In a fifth group of embodiments, five PPG parameters are employed. In one embodiment, illustrated in FIG. 7, the PPG pulse-to-pulse interval may be added to the group of parameters employed in the embodiment of FIG. 6, since PPG pulse-to-pulse interval behaves similarly as the PPG pulse amplitude with respect to pain and/or anxiety. Thus, in this particular embodiment the weighted average is calculated based on five parameters, which are the parameters used in the embodiment of FIG. 6 and the PPG pulse-to-pulse interval. As in case of PPG pulse amplitude, the time series or waveform representing the PPG pulse-to-pulse interval may be obtained from the step, in which the respiration signal(s) is/are extracted (step 72 in FIG. 7), if the said data is available in that step. Otherwise the time series or waveform representing the PPG pulse-to-pulse interval may be produced in a separate step 72$a$ based on the PPG signal data or the pre-processed PPG signal data obtained from step 31. These alternatives are not shown for the PPG pulse amplitude in FIG. 7.

Figure 8:
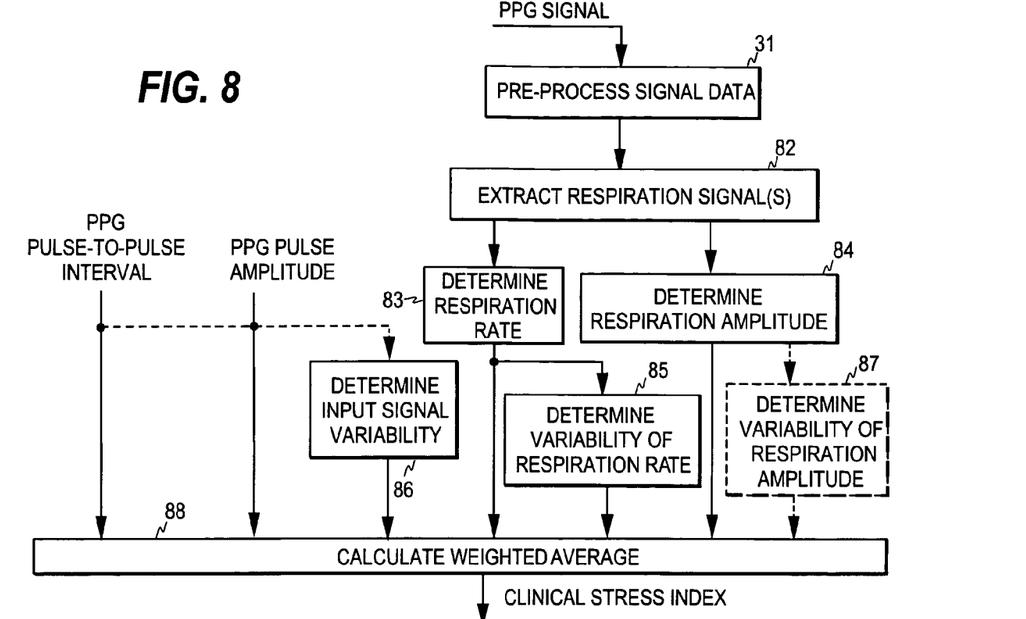

In a sixth group of embodiments, six PPG parameters are employed. As is illustrated in FIG. 8, the variability of the PPG pulse amplitude or the variability of the PPG pulse-to-pulse interval may be added to the group of PPG parameters. Thus, in this group of embodiments the weighted average is calculated based on six parameters, which are the above-mentioned five parameters of the embodiment of FIG. 7, and a sixth parameter, which may be indicative of variability in the PPG pulse amplitude or variability in the PPG pulse-to-pulse interval. As is shown in the figure, the selected input signal is supplied to step 86, in which a time series representing the variability of the input signal is determined. The variability parameter calculated may be, for example, the ratio of the low frequency variability to the high frequency variability, i.e. the so-called sympatho-vagal balance, or a ratio similar to the sympatho-vagal balance. This is due to the fact that the said low frequency variability increases and the said low frequency variability decreases when stress and/or anxiety increases.

The variability of the respiration amplitude may also be used as a PPG parameter in any of the above embodiments, in which respiration amplitude is used as a PPG parameter. This is illustrated by showing in FIG. 8 an optional step 87, in which a time series or waveform representing a parameter indicative of the variability of the respiration amplitude is produced based on the time series or waveform of the respiration amplitude.

In the above embodiments, the clinical stress index obtained may be updated for each data point of the time series, or some form of average may be calculated over a predetermined time period or over a predetermined number of weighted averages obtained.

Figure 9:
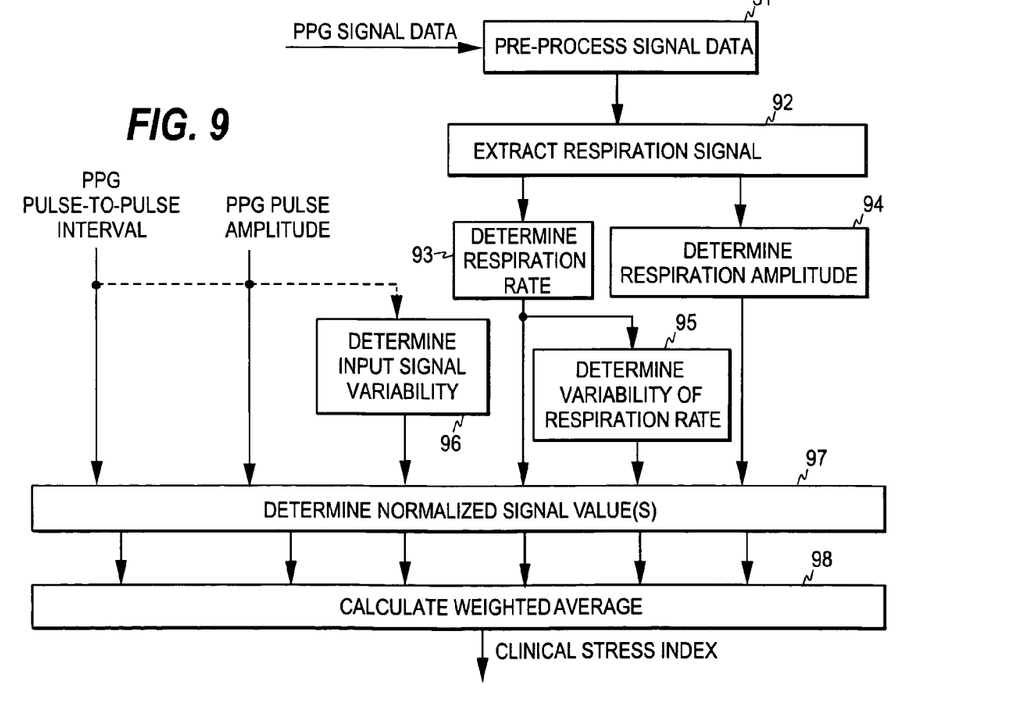

In further embodiments of the invention, one or more of the parameters used to determine the clinical stress index the may be normalized in a normalization process. As is shown in FIG. 9, the normalization process, which is denoted with reference number 97, is performed prior to the calculation of the weighted average. It is to be noted here that FIG. 9 illustrates the normalization step in connection with the embodiment of FIG. 8. The normalization step may, however, be added to any of the embodiments shown in FIG. 4 to 8. Although the normalization transform may be applied to one or more of the parameters of the respective embodiment, it is advantageous to normalize all the parameters used to calculate the weighted average in that embodiment. Furthermore, as mentioned above, step 34 in the embodiment of FIG. 3 may comprise a normalization process.

The normalization process here refers to a process that scales the input signal values to a predetermined output value range, such as 0 to 100.

The normalization process may further be patient-adaptive, i.e. it may adapt to the patient in question. In order to obtain the adaptation to the patient, the normalization transform is made dependent on time series data recorded previously for the same patient. For example, the normalization transform applied to the parameter indicative of respiration rate may be dependent on the mean and variance of the respiration rate, which are defined based on data measured earlier during a measuring period of a predetermined length, such as 5 minutes.

A third characteristic feature of a typical normalization transform is that it emphasizes slow changes in the input signal. This is accomplished by making output values that correspond to the mean or center of the input value range relatively more sensitive to input value changes than the values in the tail regions. This mechanism enhances small changes or trends in the input values and damps large, jump-like responses in the input signal. The transform is thus especially suitable for detecting relative slow changes, i.e. trends, in the patient status, such as drug affected changes in the level of antinociception.

To sum up, a typical transform applied to the respective input signal has three different properties:

the transform is a normalization transform, i.e. it forces the input values to a predetermined output value range;

the transform is patient-adaptive, i.e. it adapts to the patient and a certain index value inside the fixed range is indicative of the same amount of clinical stress for all patients; and the transform emphasizes slow changes in the input signal, which facilitates the monitoring of the trend in the clinical state.

A transform fulfilling the above criteria may be accomplished by various techniques, which include the use of a parameterized function transform or the use of a so-called histogram transform. The said two techniques are described in the following.

Figure 10:
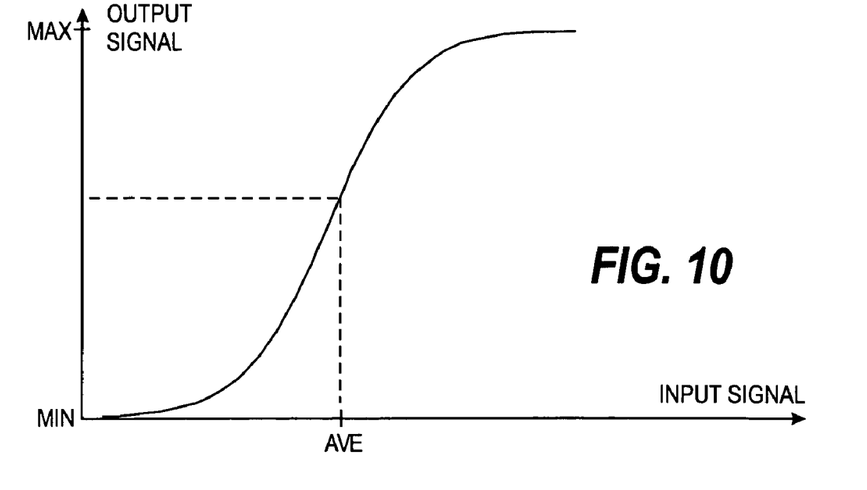
FIG. 10 illustrates typical input-output characteristics of a normalization transform that may be used in the embodiments of FIG. 3 to 9.

FIG. 10 illustrates typical input-output characteristics of the normalization transform. The curve of a typical function transform corresponds to a sigmoid function, i.e. the output value y depends on the input value x according to equation (1):

$$y = \frac{A}{1 + e^{-B*x}}, \quad (1)$$

where A and B are parameters. As discussed below, A is typically a positive constant determining the scale of the index values, while B may be a patient-specific parameter, which determines the distribution of the output index values within the scale from zero to A.

As can be seen from the figure, the transform forces the input signal to a predetermined output value range between a minimum value MIN and a maximum value MAX. For Eq. (1), MIN equals to 0, while MAX equals to A.

The adaptation to the patient may be accomplished by defining one or more patient-specific parameters and making the transform dependent on the said at least one parameter. For example, the mean <x> and standard deviation σ of the respective parameter be determined prior to the surgery based on the time series data measured during measuring period of a predetermined length, such as 5 minutes. The transform may then be made dependent on the parameters determined. For example, parameter B may be set to a value equal to the inverse of the standard deviation, i.e. B=1/σ, and the input value x may be set to a value corresponding to the difference of the current input value $x_i$ and the mean value AVE, i.e. x=$x_i$–AVE, i.e. the input value may also be dependent on previous signal data of the respective parameter.

An alternative function to Eq. (1) may be a cumulative distribution function of the Gaussian (normal) distribution function as depicted in Eq. (2):

$$f(X) = \frac{1}{\sigma\sqrt{2\pi}} \int_{-\infty}^{X} e^{-\frac{(x-<x>)^2}{2\sigma^2}} dx. \quad (2)$$

The above third feature, i.e. the emphasis of the slow changes may be accomplished by making the transform such that the slope of the transform curve is steepest around the input values that are most common, i.e. around the mean value AVE.

The output values of the transform are then used as normalized parameters, whose values define the clinical stress index.

In the above-described manner, the time series of the respective PPG parameter is transformed to a surrogate signal that has a predetermined value range and predetermined distribution characteristics for all patients. The transformation thus "forces" the values of the time series to a certain value range regardless of the incoming values, and a certain index value, such as 60, is indicative of the same amount of stress for all patients.

As discussed above, a patient-adaptive normalization transform may be implemented by using a parameterized transform including at least one patient-specific parameter. Patient-specific parameter value(s) are measured prior to the actual measurement of the stress index. The patient-specific values are then substituted for the said parameter(s) to obtain a patient-specific normalization transform. The patient-specific normalization transform is then used to transform the incoming time series to a time series containing normalized PPG parameter values.

Figure 11:
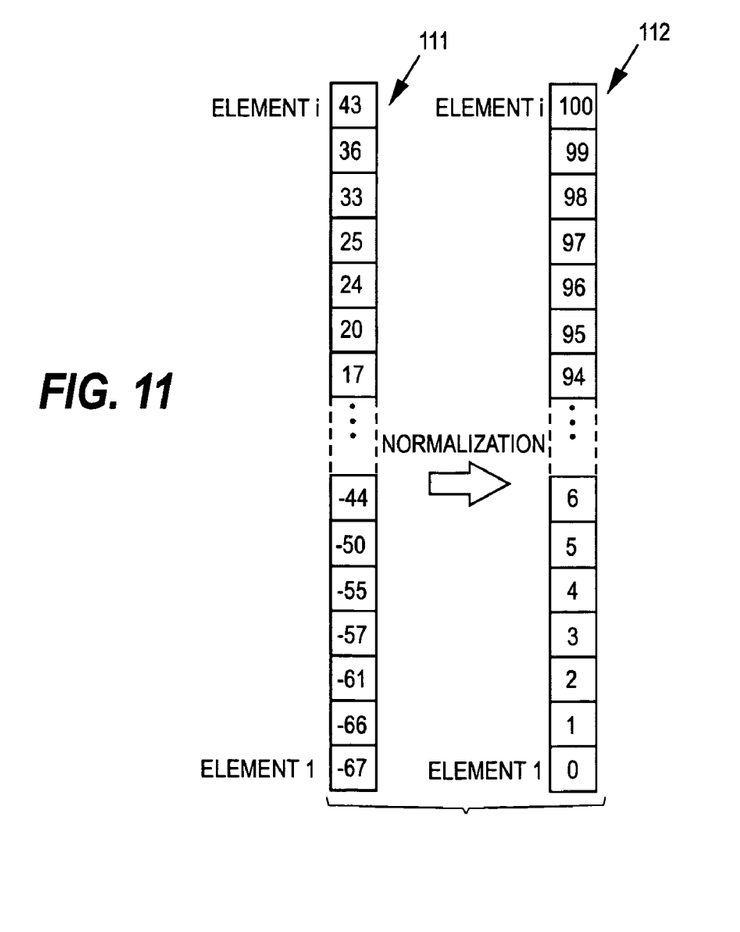
FIG. 11 illustrates the implementation of one embodiment of the normalization transform according to the invention.

Some or all of the above-described three basic properties of the transform may also be achieved by using a histogram transform. In a histogram transform, an input array 111 and an output array 112 are formed, as is shown in FIG. 11. The input array (buffer) comprises i input elements, also termed bins, storing, respectively, i input values sorted in ascending or descending order, while the output array (buffer) comprises fixed index values sorted in ascending or descending order and stored in i output elements. In the example of FIG. 11, the index values of the output buffer range from 0 to 100 corresponding to the total number of values in the input buffer, i.e. i=101. The values of the time series of the PPG parameter are thus forced to the value range of the output buffer. This may be implemented in three different ways depending on whether full adaptation, partial adaptation, or no adaptation to the incoming signal is utilized. These embodiments of the histogram transform are discussed briefly in the following.

In full adaptation, the latest signal values of the time series of the respective PPG parameter are stored in the input array so that the value of each new data point obtained in the time series replaces the oldest value in the input array. When a new PPG parameter value is obtained, the oldest value in the input array is deleted, and the remaining values and the new value are sorted to form a new input array. The output value of the transform is then obtained by means of the output array as the index value that corresponds to the location of the new value in the input array. In this way, the level of the signal may change but the output values remain between the lowest and highest indices, i.e. in this example between 0 and 100. The time series obtained from the output array 112 may thus be such that the mean value is constant and the variability of the amplitude is limited to a certain range and certain distribution around the mean value. For instance, a Gaussian or even distribution with a desired mean value may be used for the values output from the transform.

Full adaptation may also be implemented by a parameterized transform. If a histogram transform is used, no patient-specific parameters are needed, since the sorting of previous signal data makes the histogram transform patient-adaptive. If a parameterized transform is used, no sorting of input data is needed.

In case no adaptation to the incoming signal is used in the histogram transform, the input array remains the same regardless of the incoming signal values. The input array may be formed based on values measured from a certain patient group or in certain measurement set-up, which yields a wider distribution of input values than what is typically obtained for one patient or set-up. Thus, instead of storing the latest i values of the same patient, the input array may store i fixed values representing the distribution of the values of the PPG parameter among a (large) group of patients. When a new value is obtained in the incoming time series of the PPG parameter, the corresponding output value of the transformation is obtained in the above-described manner as the index value that corresponds to the location of the new value in the sorted input array. Although this embodiment of the histogram transform is not patient-adaptive, different input arrays may still be defined for different patient groups, such as children or adults, and different input arrays may further be defined for each patient group according to various other parameters, such as the type of the sensor used or the peripheral site of the sensor (ear, finger, toe).

Similar non-adaptive transforms may be implemented by means of the parameterized transform. In this case the transform includes one or more parameters, whose value(s) depend on the patient group in question, and possible also on other parameters, such as the sensor type or site.

Figure 12A:
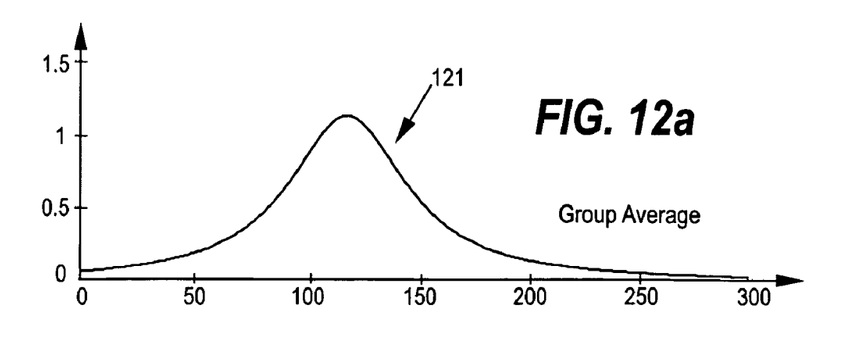
FIG. 12a to 12d illustrate one embodiment of the normalization transform of the invention.
Figure 12B:
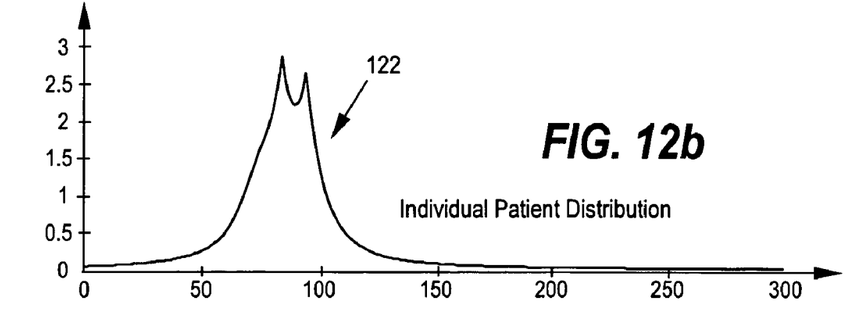
Figure 12C:
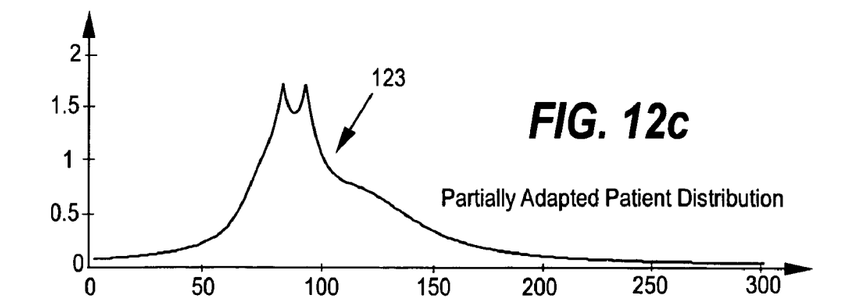
Figure 12D:
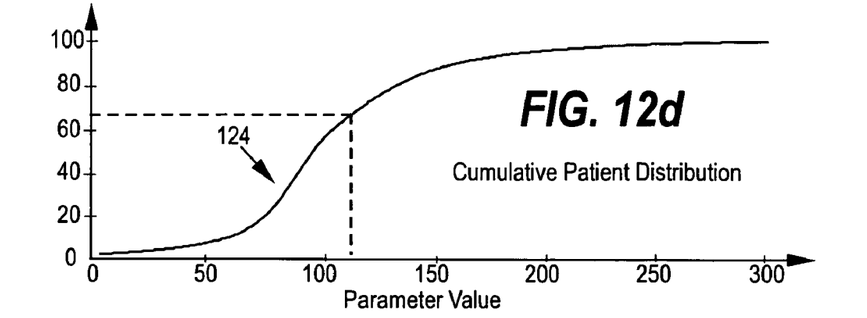

Partial adaptation to the incoming signal refers to the combination of the above two methods. An embodiment of the partial adaptation is illustrated in FIG. 12a to 12d. FIG. 12a illustrates a parameter distribution curve 121 for a large number of patients representing a certain patient group in general anesthesia. The size of the patient group may be very large representing about 1000 patients, for example. The range of the parameter values, in the figures from 0 to 300, is advantageously selected to be much wider than the actual range obtained for an individual patient. Later the same PPG parameter, such the respiration rate or the variability of the respiration rate, is measured and a histogram distribution is created using the same parameter value bins as in the large population average. This distribution for the individual patient may contain a fixed number of values, e.g. 300, and the distribution may be updated using the full adaptation method described above. It is also possible that a cumulative distribution of the parameter values of the individual patient is collected and that the distribution counts so obtained are scaled down to a predetermined match in total counts to the patient group distribution. In such a case, the individual patient distribution may represent the parameter values since the beginning of the monitoring till the current moment during monitoring. An example of a normalized patient-specific distribution curve 122 obtained during a surgery is presented in FIG. 12b The normalized patient-specific distribution is then added in a predetermined proportion to the normalized patient group distribution, and an average total distribution curve 123 is formed, as shown in FIG. 12c. In this example, the two normalized distributions are weighted equally in the total distribution. For calculating the input parameter value array for the partially adapted histogram transform a cumulative sum of the average total distribution is then constructed as shown in FIG. 12d. If the histogram transform arrays are 101 element long, for example, the new values for the input bins of the histogram transform can be obtained by projecting the cumulative sum values 0, 1, 2, . . . , 100 of the Y-axis to the parameter value axis (X-axis), as is shown by dashed lines in FIG. 12d. The X-axis values obtained in this way form the input values of the input array for the histogram transform. The actual histogram transform is then executed without adaptation. In this embodiment, input values for the input array are thus obtained by adding a group distribution curve to the patient-specific distribution curve and then defining the input values for the input array by means of the cumulative distribution function of the summed distribution curve. Once being defined in the above-described manner, the input values of the input array remain fixed for a predetermined update interval, which can typically represent about 100 new individual parameter values.

The proportions of the adaptive and non-adaptive values in the combined input may vary. The same applies to the size of the steps between consecutive (fixed) values stored in the input or output arrays. For example, in the example presented in connection with FIG. 12a to 12d each consecutive input array bin contained one percent of the input values. However, the steps may also be such that a certain other percentage of values is within each step (i.e. in each bin), in which case the step may be smaller around one range of the input values and correspondingly larger around another range of the input values. The median value of the output signal, i.e. the center index of the output array, may be transformed to a desired output value, such as 50. The distribution of the output values may be specified according to the needs of the application.

As the adaptation to the patient is a preferred property for the normalization transform, fully or partially adaptive normalization transforms are the preferred transforms to be applied to the PPG parameter(s). As discussed above, in case of a partially adaptive transform, the normalization transform to be used at each time may depend on the patient, i.e. to which patient group the patient belongs, on the sensor used, and/or on the location of the sensor (finger or ear).

A generalized form of a partial patient adaptive histogram transformation may thus be presented as follows: H(patient adaptive transformation)=A*H1 (large patient population)+ B*H2(history data since the beginning of the monitoring)+ C*H3(history data over the last M minutes), in which the first reference histogram H1 is for a large population group of similar patients (adults, children, infants, etc.) or for a particular type of sensor or equipment (PPG finger sensor, PPG ear sensor, etc.), the second reference histogram H2 is for the parameter values recorded since the beginning of monitoring or anesthesia (long history data), and the third reference histogram H3 is for the parameter values recorded over the last M minutes, such as 5 minutes (short history data). The multiplying factors (A, B, and C, where A+B+C=1) are the relative weights of the separately normalized histogram distributions. The principal reason for the usage of a patient population histogram is that it contains the widest distribution of the parameter values, and thereby represents the allowable parameter range of the input values. The history data since the beginning of the monitoring substantially sets each patient to the same norm. The histogram pertaining to the last M minutes allows a fast adaptation to trend-like parameter changes within one patient and thereby sets each phase of the monitoring to a same equivalent norm, regardless of the absolute average value of the parameter in the time window of M minutes.

Partial adaptation may also be implemented by a parameterized transform. In this case, the transform includes both patient-specific and group-specific parameters in a fashion similar to the above histogram transformation. The parameters may be defined in various ways. For instance, the mean parameter in the function transform may be determined as a weighted mean of the mean values of the parameter in a large patient group data, in the long history data, and in the short history data of M minutes, while the variance parameter in the function transform may be determined as a weighted sum of the variances obtained from the two groups of history data.

Figure 13:
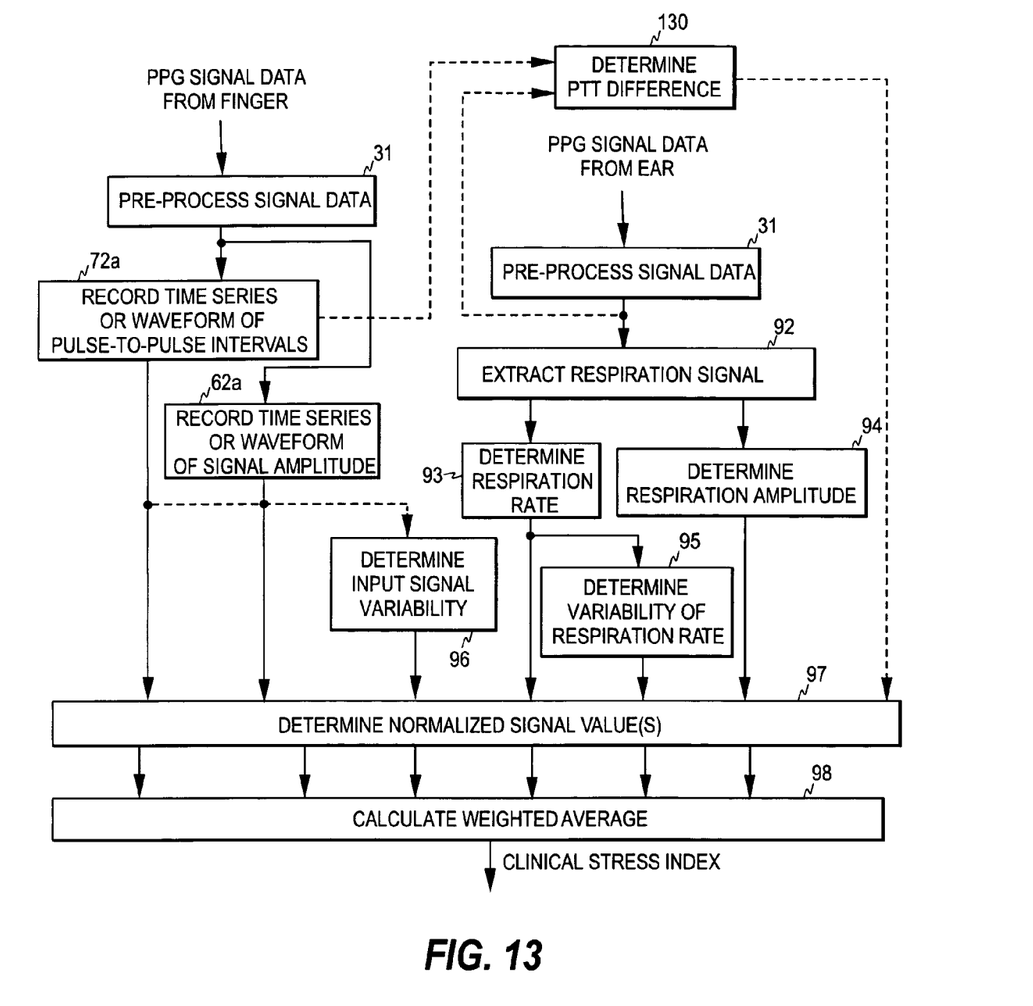
FIG. 13 illustrates an embodiment, in which the plethysmographic signal data is measured from two sensor sites of a patient.

In one embodiment of the invention, two PPG waveforms may be recorded simultaneously from two different body parts, for instance from finger and ear. FIG. 13 illustrates the embodiment of FIG. 9 when the PPG signal data is acquired both from an ear sensor and from a finger sensor. Typically, the respiration modulation of the PPG amplitude and the baseline DC signal are relatively larger in ear than in finger. Furthermore, as the movement artefacts are much less frequent and smaller in a PPG signal measured from ear, the respiration signal is less corrupted and easier to detect from ears. Sometimes also the so-called Mayer wave or a vasomotor wave may be so strong and have nearly the same period as the respiration signal that it harms the detection of the respiration signal considerably. The Mayer wave appears differently on different sensor sites, and the detection of the respiration signal may therefore be less disturbed on the sensor site, which has a relatively smaller Mayer wave component. Because the PPG amplitude in ears is smaller than in fingers, the detection of the PPG amplitude is easier from fingers. Therefore, the respiration rate and the respiration amplitude may be determined from an ear signal and the finger signal may be used for the PPG amplitude and the pulse-to-pulse interval. A better signal quality is thus achieved, as each PPG parameter is detected from the site, which has a better signal quality for the particular parameter.

A further advantage of using PPG waveforms recorded simultaneously at two sites is that the physiological information is different on different sites. For instance, vasoconstriction has a much stronger effect on the finger PPG waveform than on the ear one. Since vasoconstriction is caused by sympathetical activation, it is preferable to determine the sympathetical activation based on the finger signal PPG amplitude.

It is also possible that the PPG amplitudes obtained from different sensor sites are compared with each other. This helps to eliminate the reasons, which affect the signal similarly, and allows the signal to be selected that provides the most reliable and/or specific determination of the clinical stress index. Another effect of the sympathetical activation or vasoconstriction is that the pulse transit time (PTT), i.e. the time interval between the actual heart beat and the pressure pulse in the peripheral body part, changes differently in the two body sites. The PTT to ears is considerably shorter and more constant than to fingers. In a further embodiment of the invention, the signals and signal parameters, such as PTT, PPG amplitude and respiration modulation, obtained from finger originated plethysmographic data and from ear originated plethysmographic data may thus be compared and additional and/or complementary information may be determined for the clinical stress status based on the differences. FIG. 13 illustrates an example in which a measure indicative of PTT difference is determined at step 130 by determining the time difference between corresponding amplitude peaks in the ear and finger originated signal data. The said measure may be used as a PPG parameter for calculating the index, since it is indicative of sympathetical activation. The selection of the sensor may also be based on the above-mentioned comparison of the ear and finger signals.

Since the stress index determination process of the invention requires a minimum of one channel, i.e. the signal data of the R (red) channel or the IR (infrared) channel, the above two sensor site apparatus may also be a standard pulse oximeter, which is configured to act as a two site plethysmograph in which one channel is for the ear and the other for the finger plethysmograph, both using the same IR wavelength. In this configuration, the detector is split between the sites, for instance using two detectors in parallel.

Although the invention was described above with reference to the examples shown in the appended drawings, it is obvious that the invention is not limited to these, but may be modified by those skilled in the art without departing from the scope and spirit of the invention.

The invention claimed is:

1. A method for determining clinical stress of a subject, the method comprising the steps of:
    positioning a probe of a pulse oximeter on the subject;
    acquiring plethysmographic signal data from the pulse oximeter associated with a subject;
    deriving a first measurement signal in a control and processing unit, the first measurement signal being indicative of a predetermined feature of respiration modulation appearing in the plethysmographic signal data, wherein the deriving step includes deriving the first measurement signal indicative of the predetermined feature, in which the predetermined feature is the respiration rate;
    forming an index signal in the control and processing unit based on the first measurement signal, wherein the forming step includes a sub-step of generating a second measurement signal indicative of variability in the first measurement signal; and
    employing the index signal as an index indicative of the clinical stress of the subject.

2. A method according to claim 1, wherein the forming step further includes applying a second normalization transform to the second measurement signal, the second normalization transform being dependent on predetermined second history data, whereby a second normalized measurement signal having a predetermined value range is obtained, the second normalized measurement signal being the index signal.

3. A method according to claim 1, wherein the forming step includes forming the index signal, in which the index signal is indicative of a change in the second measurement signal.

4. A method according to claim 1, wherein the forming step further includes a sub-step of calculating a weighted average of the first measurement signal and the second measurement signal, the weighted average forming the index signal.

5. A method according to claim 1, further comprising the steps of:
    applying a first normalization transform to the first measurement signal, the first normalization transform being dependent on predetermined first history data, whereby a first normalized measurement signal having a predetermined value range is obtained; and
    applying a second normalization transform to the second measurement signal, the second normalization transform being dependent on predetermined second history data, whereby a second normalized measurement signal having a predetermined value range is obtained.

6. A method according to claim 5, wherein the forming step further comprises a sub-step of calculating a weighted average of the first normalized measurement signal and the second normalized measurement signal, the weighted averave forming the index signal.

7. A method according to claim 1, further comprising a step of producing at least one further measurement signal from the plethysmographic signal data, wherein the at least one further measurement signal belongs to a group of signals including a first signal indicative of respiration amplitude, a second signal indicative of variability in the respiration amplitude, a third signal indicative of pulse amplitude in the plethysmographic signal data, a fourth signal indicative of pulse-to-pulse interval in the plethysmographic signal data, and a fifth signal indicative of variability in one of the third and fourth signals.

8. A method according to claim 7, wherein the forming step includes calculating a weighted average of the first measurement signal, the second measurement signal, and the at least one further measurement signal, the weighted averave forming the index signal.

9. A method according to claim 7, further comprising the steps of:
    applying a first normalization transform to the first measurement signal, the first normalization transform being dependent on predetermined first history data, whereby a first normalized measurement signal having a predetermined value range is obtained;
    applying a second normalization transform to the second measurement signal, the second normalization transform being dependent on predetermined second history data, whereby a second normalized measurement signal having a predetermined value range is obtained; and
    applying a dedicated normalization transform to each of the at least one further measurement signal, each dedicated normalization transform being dependent on predetermined history data specific to the dedicated normalization transform concerned, whereby at least one further normalized measurement signal having a predetermined value range is obtained.

10. A method according to claim 9, wherein the forming step includes calculating a weighted average of the first normalized measurement signal, the second normalized measurement signal, and the at least one further normalized measurement signal, the weighted averave forming the index signal.

11. A method according to claim 7, wherein the acquiring step includes measuring the plethysmographic signal data from an ear and from a finger of the subject, whereby the plethysmographic signal data comprises ear originated signal data and finger originated signal data.

12. A method according to claim 11, further comprising the steps of:
   comparing the ear originated signal data with the finger originated signal data; and
   selecting whether the ear originated signal data or the finger originated signal data is to be employed for the first measurement signal and whether the ear originated signal data or the finger originated signal data is to be employed for at least one of the third, fourth, and fifth signals.

13. A method according to claim 11, further comprising a step of determining a transit time difference indicative of the time difference between corresponding signal peaks in the ear originated signal data and in the finger originated signal data.

14. A method according to claim 1, further comprising a step of controlling administration of at least one drug to the subject, wherein the controlling step is performed based on the index signal and the at least one drug is selected from a group of drugs including at least one analgesic drug and at least one sedative drug.

15. A method according to claim 1, further comprising a step of producing at least one further measurement signal from the plethysmographic signal data, wherein the at least one further measurement signal belongs to a group of signals including a first signal indicative of respiration amplitude, a second signal indicative of variability in the respiration amplitude, a third signal indicative of pulse amplitude in the plethysmographic signal data, a fourth signal indicative of pulse-to-pulse interval in the plethysmographic signal data, and a fifth signal indicative of variability in one of the third and fourth signals.

16. A method according to claim 15, wherein the acquiring step includes measuring the plethysmographic signal data from an ear and from a finger of the subject, whereby the plethysmographic signal data comprises ear originated signal data and finger originated signal data.

17. A method according to claim 16, further comprising the steps of:
   comparing the ear originated signal data with the finger originated signal data; and
   selecting whether the ear originated signal data or the finger originated signal data is to be employed for the first measurement signal and whether the ear originated signal data or the finger originated signal data is to be employed for at least one of the third, fourth, and fifth signals.

18. A method according to claim 16, further comprising a step of determining a transit time difference indicative of the time difference between corresponding signal peaks in the ear originated signal data and in the finger originated signal data.

19. A method for determining clinical stress of a subject, the method comprising the steps of:
   positioning a probe of a pulse oximeter on the subject;
   acquiring plethysmographic signal data from the pulse oximeter associated with a subject;
   deriving a first measurement signal in a control and processing unit, the first measurement signal being indicative of a predetermined feature of respiration modulation appearing in the plethysmographic signal data;
   producing at least one further measurement signal in the control and processing unit from the plethysmographic signal data, wherein the at least one further measurement signal belongs to a group of signals including a first signal indicative of respiration amplitude, a second signal indicative of variability in the respiration amplitude, a third signal indicative of pulse amplitude in the plethysmographic signal data, a fourth signal indicative of pulse-to-pulse interval in the plethysmographic signal data, and a fifth signal indicative of variability in one of the third and fourth signals;
   forming an index signal in the control and processing unit based on the first measurement signal; and
   employing the index signal as an index indicative of the clinical stress of the subject.

* * * * *

UNITED STATES PATENT AND TRADEMARK OFFICE
CERTIFICATE OF CORRECTION

PATENT NO. : 7,635,337 B2
APPLICATION NO. : 11/089548
DATED : December 22, 2009
INVENTOR(S) : Huiku et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1207 days.

Signed and Sealed this

Ninth Day of November, 2010

David J. Kappos
*Director of the United States Patent and Trademark Office*